US009153426B2

(12) United States Patent
Cichon, Jr.

(10) Patent No.: US 9,153,426 B2
(45) Date of Patent: Oct. 6, 2015

(54) DEVICES AND METHODS FOR FACILITATING TREATMENT OF ELECTROSPRAY COLUMNS

(71) Applicant: Regeneron Pharmaceuticals, Inc., Tarrytown, NY (US)

(72) Inventor: Samuel E. Cichon, Jr., Fishkill, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 146 days.

(21) Appl. No.: 14/104,729

(22) Filed: Dec. 12, 2013

(65) Prior Publication Data

US 2015/0165598 A1   Jun. 18, 2015

(51) Int. Cl.
*H01J 49/10* (2006.01)
*H01J 49/16* (2006.01)

(52) U.S. Cl.
CPC .................................. *H01J 49/167* (2013.01)

(58) Field of Classification Search
CPC ....................................................... H01J 49/167
See application file for complete search history.

(56) References Cited

U.S. PATENT DOCUMENTS 7,641,242 B2 *   1/2010   Van Pelt .................. 285/384
2014/0305801 A1 *  10/2014   Peterson et al. .......... 204/604

FOREIGN PATENT DOCUMENTS

WO     WO 2013167131 A1 *  11/2013

* cited by examiner

*Primary Examiner* — Jack Berman
(74) *Attorney, Agent, or Firm* — Heslin Rothenberg Farley & Mesiti, P.C.

(57) ABSTRACT

The present disclosure generally provides devices and methods for facilitating treatment of a tip portion of an emitter of an electrospray column. The column includes a sheath at a distal end that is normally biased in an extended position that covers the tip portion, and is in a retracted positioning during use that exposes the tip portion. The devices of the present disclosure provide a longitudinally extending support member, a laterally extending sheath engagement member, and a laterally extending column engagement member. The devices are configured such that when the devices and column are coupled, the column engagement member of the device engages a lateral surface at a proximal portion of the column, and the sheath engagement member engages and retracts the distal sheath of the column to expose the tip portion of the emitter.

21 Claims, 12 Drawing Sheets

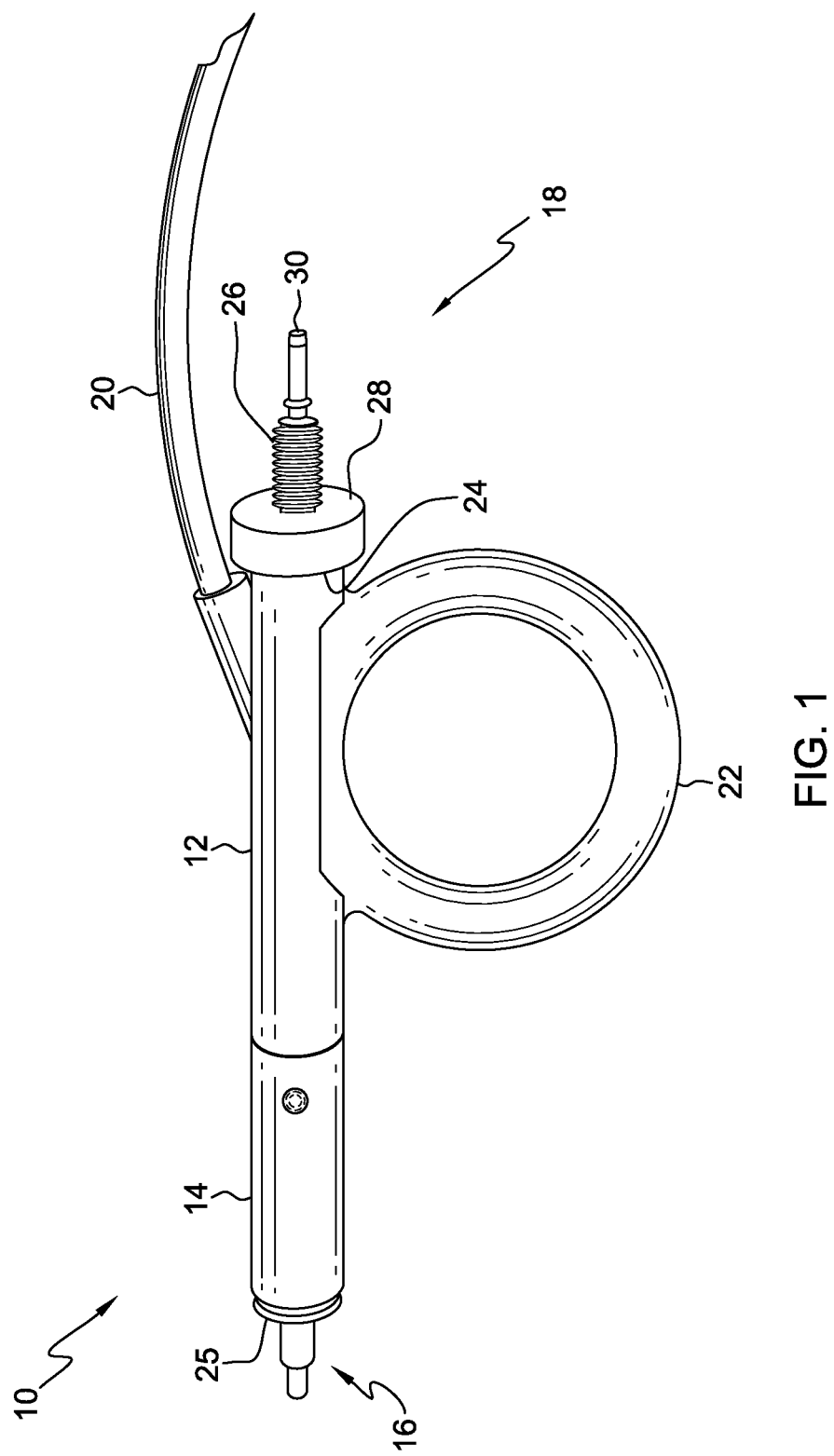

DEVICES AND METHODS FOR FACILITATING TREATMENT OF ELECTROSPRAY COLUMNS

FIELD OF THE DISCLOSURE

The present disclosure generally relates to devices and methods for facilitating treatment of a spray column. More particularly, the present invention relates to devices and methods for facilitating treatment of a tip portion of an emitter of an electrospray column.

BACKGROUND

Liquid chromatography-mass spectrometry (LC-MS, or alternatively HPLC-MS) is a chemistry technique that combines the physical separation capabilities of liquid chromatography (or HPLC) with the mass analysis capabilities of mass spectrometry. LC-MS is a powerful technique used for many applications which has very high sensitivity and selectivity. Generally its application is oriented towards the general detection and potential identification of chemicals in the presence of other chemicals (in a complex mixture).

Electrospray ionization is a typical ion source that couples liquid chromatography with mass spectrometry. Electrospray ionization is also utilized in many other applications. In the electrospray ionization, liquid eluting from a chromatography column is either part of, or attached to, an emitter which has an emitter or spray tip of a diameter less than about 10 um. Electrospray formed from columns with emitters or spray tips that are fabricated by pulling glass capillaries to a few micrometers is commonly referred to as nano-electrospray or nanospray. For the production of positive ions, liquid that is forced through emitters of columns is subjected to relatively high voltage either upstream of the emitter tip or by coating the emitter (to the emitter tip and in contact with the liquid) in an electrically conductive substance. In this way, electrospray ionization induces the formation of a spray of positively charged droplets generated at the emitter tip.

As the emitter or spray tip of a chromatography and/or mass spectrometry electrospray column (e.g., a nanospray column) is a relatively delicate, expensive, small scale, highly precise and potentially hazardous component, the emitter or spray tip is typically protected by a sheath or sleeve. The protective sheath or sleeve of the column is retracted or otherwise translated away from the tip of the emitter such that at least the emitter tip is exposed during use. When not in use, however, the protective sheath or sleeve extends over the emitter tip or spray tip and an adjacent portion of the emitter to protect the emitter tip portion from damage or contamination, and to protect users from both accidental pricks and exposure to potentially hazardous materials provided in or on the emitter. In such a protective position or arrangement, the protective sheath or sleeve prevents both visual and tactile treatment of the emitter tip portion.

Treatment of the emitter tip portion may be desirable both before and after use. Specifically, it may be desirable to visually and/or tactilely treat the emitter tip portion before and after use. For example, visual inspection of the emitter tip portion may be desirable to check for damage (e.g., cracks, chips, etc.), defects, clogs or any other condition which would negatively affect the performance of the column (e.g., the spray emanating from the tip). Similarly, physical cleaning and/or inspection of the emitter tip portion may be necessary or desirable to ensure proper or adequate performance of the column.

The protective sheath or sleeve of the column makes such treatment difficult and dangerous to both the user and the emitter tip portion itself. For example, to treat an emitter tip portion before or after use of the column, a user must manually retract or otherwise move or remove the protective sheath or sleeve into a non-protective position. This is typically accomplished via one or more finger of the user, or through the use of a foreign tool or the like. Further, the user must manually maintain the retracted or non-protective position of the sheath or sleeve during treatment. Such a manual process is not only difficult, tedious and inconvenient, it is dangerous to the user and the emitter tip portion. Needle pricks, hazardous material exposure, and damage to the emitter tip portion and/or the protective sheath is likely to occur when the protective sheath is manually retracted or otherwise moved into a non-protective position, and maintained in such a position during visual and/or tactile treatment of the emitter tip portion.

As a result, a need exists for devices and methods that facilitate treatment of electrospray columns and like devices to reduce or substantially eliminate the risk of needle pricks, hazardous material exposure, and damage to the emitter tip portion and/or the protective sleeve or sheath during treatment.

BRIEF DESCRIPTION

In one aspect, a device for facilitating treatment of an electrospray column is disclosed. The electrospray column may include a protective sheath that protects a tip portion of an emitter of the column in a first longitudinally extended position and exposes the tip portion in a second longitudinally retracted position. The device may include a substantially longitudinally extending support member, a sheath engagement member, and a column engagement member. The sheath engagement member may be positioned at a distal portion of the support member and configured to engage the protective sheath of the column. The column engagement member may be positioned at a proximal portion of the support member and configured to engage a laterally extending portion of the column. The longitudinal spacing of the sheath engagement member and the column engagement member may be configured to position the protective sheath in the second longitudinally retracted position to expose the tip portion of the emitter of the column when the sheath engagement member engages the protective sheath of the column and the column engagement member engages the laterally extending portion of the column.

In some embodiments, the longitudinally extending support member includes an interior surface configured to engage an exterior surface of the column when the sheath engagement member and the column engagement member engage their respective portions of the column. In some such embodiments, the interior surface of the longitudinally extending support member is a substantially laterally-facing arcuate surface. In some such embodiments, the interior surface of the longitudinally extending support member forms a cavity configured to receive a portion of the column therein when the sheath engagement member and the column engagement member engage their respective portions of the column. In some such embodiments, the cavity is substantially cylindrical.

In some embodiments, the sheath engagement member includes an aperture configured to engage the protective sheath of the column. In some such embodiments, the aperture of the sheath engagement member is configured to allow a narrow portion of the protective sheath of the column to least extend into the aperture and to prevent a wide portion of the protective sheath of the column from extending into the aperture.

In some embodiments, the sheath engagement member is substantially laterally extending and configured to engage a laterally extending portion of a wide portion of the protective sheath of the column and allow a narrow portion of the protective sheath extend at least partially pass through the sheath engagement member. In some embodiments, the sheath engagement member is substantially laterally extending and configured to engage a distal end of the protective sheath of the column.

In some embodiments, the device includes a handle extending from a proximal portion of the support member. In some such embodiments, the handle extends laterally from a first portion of an exterior surface of the support member and distally toward the sheath engagement member. In some such embodiments, the handle is substantially arcuate. In some other such embodiments, the handle includes a substantially laterally extending member and a substantially longitudinally extending member. In some such embodiments, the column engagement member is substantially laterally extending and positioned on the laterally extending member.

In some embodiments, the device includes a laterally extending projection extending from a distal portion of the first portion of the exterior surface of the support member. In some embodiments, the column engagement member is substantially laterally extending and positioned on a proximal end of the support member. In some embodiments, the column engagement member includes a substantially laterally extending relief.

In another aspect, a method of temporality retracting a protective sheath of an electrospray column to expose a tip portion of an emitter of the column is disclosed. The method may include providing or obtaining a device including a substantially longitudinally extending support member, a sheath engagement member at a distal portion of the support member, and a column engagement member at a proximal portion of the support member. The method may further include engaging a portion of the protective sheath of the column with the column engagement member of the device. The method may further include translating at least one of the column and the device with respect to one another such that the sheath engagement member translates the protective sheath into a retracted position that exposes the tip portion of the emitter of the column. The method may further include engaging a laterally extending portion of the column with the column engagement member to couple the column and the device with one another and to maintain the protective sheath in the retracted position to expose the tip portion of the emitter of the column.

In some embodiments, engaging a portion of the protective sheath of the column with the column engagement member of the device includes positioning a narrow portion of the protective sheath within an aperture of the column engagement member and engaging a wide portion of the protective sheath with the aperture. In some embodiments, the device includes a laterally and distally extending handle extending from an external surface of the support member, and method includes positioning the coupled device and column on a substrate by positioning the handle of the device over a top edge of a substrate such that the exterior surface of the support member is positioned on one side of the substrate and at least a portion of the handle is positioned on an opposing side of the substrate. In some embodiments, the method includes treating the exposed tip portion of the emitter of the column. In some embodiments, the laterally extending portion of the column is a proximal end of a holding portion of the column or an extension portion of the holding portion.

These and other objects, features, and advantages of this disclosure will become apparent from the following detailed description of the various aspects of the disclosure taken in conjunction with the accompanying drawings.

DRAWINGS

FIG. 1 is a side view of an exemplary electrospray column in accordance with an exemplary embodiment of the present disclosure;

DETAILED DESCRIPTION

Each embodiment presented below facilitates the explanation of certain aspects of the disclosure, and should not be interpreted as limiting the scope of the disclosure. Moreover, approximating language, as used herein throughout the specification and claims, may be applied to modify any quantitative representation that could permissibly vary without resulting in a change in the basic function to which it is related. Accordingly, a value modified by a term or terms, such as "about," is not limited to the precise value specified. In some instances, the approximating language may correspond to the precision of an instrument for measuring the value. When introducing elements of various embodiments, the articles "a," "an," "the," and "said" are intended to mean that there are one or more of the elements. The terms "comprising," "including," and "having" are intended to be inclusive and mean that there may be additional elements other than the listed elements. As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances, the modified term may sometimes not be appropriate, capable, or suitable. Any examples of operating parameters are not exclusive of other parameters of the disclosed embodiments. Components, aspects, features, configurations, arrangements, uses and the like described, illustrated or otherwise disclosed herein with respect to any particular embodiment may similarly be applied to any other embodiment disclosed herein.

Figure 2A:
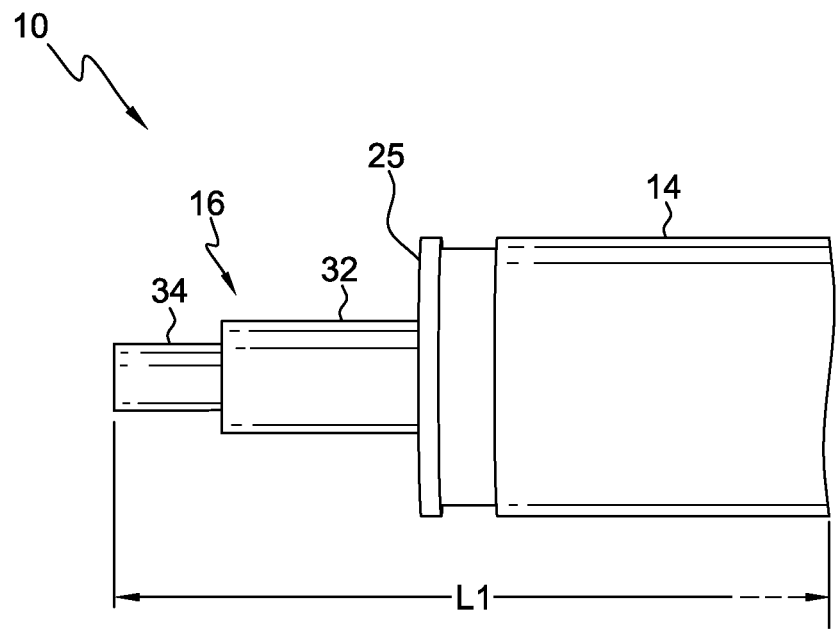
FIGS. 2A and 2B are side views of the protective sheath of the exemplary electrospray column of FIG. 1 in an exemplary extended protective position and an exemplary retracted unprotective position, respectively, in accordance with an exemplary embodiment of the present disclosure.

FIGS. 1-2A illustrate an exemplary chromatography column 10 that may be utilized with the devices, systems and methods of the present disclosure. The exemplary column 10 may be configured to be utilized in LC-MS. As shown in FIG. 1, the exemplary column 10 may be an integrated column-emitter combination design. The column 10 may include an exemplary column holding and/or heating portion 12, an exemplary metal or conducting portion 14, an exemplary sheath or sleeve portion 16, an exemplary fitting portion 18, and an exemplary electrical connection 20. The exemplary column 10 may include an emitter extending within the metal portion 14 and the sheath portion 16, as discussed further herein. The metal portion 14 may provide a voltage connection to eluent within the emitter. The sheath portion 16, metal portion 14, column holding portion 12 and fitting portion 18 may be arranged and shaped such that the column is generally elongate along a longitudinal direction. For example, the sheath portion 16, metal portion 14, cylindrical holding portion 12 and fitting portion 18 may form a longitudinally extended column shape, with at least some of the portions defining differing widths or diameters in a lateral direction, as shown in FIG. 1. In some embodiments, the column 10 may be the EASY-Spray™ column sold by Thermo Fisher Scientific™ Inc. The terms "longitudinally" and "laterally" (and the like) are meant herein as reference directions (or planes) and are not meant and used herein in a limiting sense. As used herein, the lateral direction (or plane) may be any direction (or planes) that intersects, or is angled with respect to, the longitudinal direction (or plane) (i.e., is not parallel with the longitudinal direction). For example, the lateral direction (or plane) may extend in a direction that is substantially perpendicular (or normal), or angled 90 degrees, with respect to the longitudinal direction (or plane).

As also shown in FIG. 1, the column holding portion 12 may include an extension portion 22 that extends or is positioned generally laterally from the longitudinally extending column 12. The extension portion 22 may allow the column 10 to hold additional column material. In the exemplary embodiments shown in FIGS. 3-6, the extension portion 22 is generally arcuate or circular with an aperture therethrough, and is generally positioned laterally from the longitudinally-extending column 12. In such an embodiment, the arcuate extension portion 22 may allow additional column material to be coiled within the column holding portion 12.

The column portion 12 of the column 10 may include a laterally extending proximal or top edge or surface 24 that is adjacent the fitting portion 18 in the longitudinal direction, as shown in FIG. 1. The laterally extending proximal or top edge or surface 24 of the column 10 may be provided on a proximal portion of the device 110 in the longitudinal direction. As also shown in FIG. 1, the metal portion 12 of the column 10 may include a laterally extending distal or bottom edge or surface 25 that is adjacent the sheath 16 in the longitudinal direction. The laterally extending distal or bottom edge or surface 25 may be provided on a distal portion of the device 110 in the longitudinal direction. As discussed above, the term "proximal or "proximate" and "distal" are meant herein as reference positions or directions in the longitudinal direction and are not meant in a limiting sense.

As also shown in FIG. 1, the exemplary fitting portion 18 may include an externally threaded portion 26, a nut 28 threadably coupled to the threaded portion 26, and a channel portion 30 that provides a pathway to the interior of the to the column holding portion 12. In this way, the fitting portion 18 may allow a source of column material to be coupled to the column 10 via a fitting. In some embodiments, the fitting portion 18 may be configured to couple the column 10 with a NanoViper™ fitting sold by Thermo Fisher Scientific™ Inc.

Figure 2B:
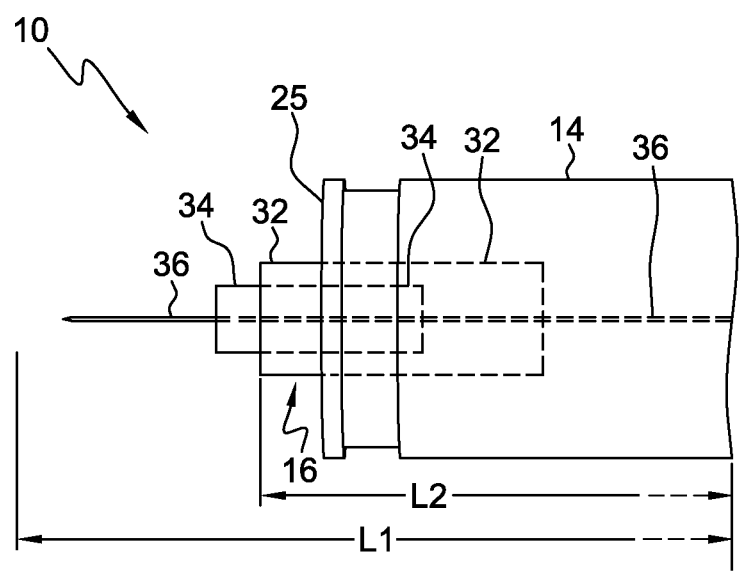

With reference to FIGS. 2A and 2B, the sheath or sleeve portion 16 may protect an emitter 36 extending in the metal portion 14 and, potentially, the column holding portion 12. The emitter 36 (FIG. 2B) may be a glass emitter that defines a flow path of a few micrometers or less. An electrospray may emanate from the tip of the emitter 36 during use. The emitter 36 may be substantially precise, fragile, sharp and contain hazardous material. The sheath or sleeve portion 16 may protect the spray tip of the emitter 36 and a portion of the emitter adjacent thereto (hereinafter referred to as the "tip portion" of the emitter 36), as shown in FIG. 2A, in an extended position. In the extended position, the sheath 16 may substantially surround the tip portion of the emitter 36 and extend past the free tip or end of the emitter 36. In this way, the extended position of the sheath or sleeve portion 16 of the column 10 may protect the tip portion of the emitter 36 from damage and contamination (and protect a user form the tip portion of the emitter 36) when the column 10 is not in use (i.e., coupled with a liquid chromatography and/or mass spectrometer component).

In contrast, as shown in FIG. 2B, in a retracted position the sheath or sleeve portion 16 may expose the tip portion of the emitter 36. In some embodiments, the sheath 16 may extend past the free tip or end of the emitter 36 and include an end cap, portion or member that includes an aperture to allow the emitter 36 to pass through the aperture when the sheath 16 in a retracted position. In other embodiments, the sheath 16 may include an opening that is positioned past the tip of the emitter 36 when the sheath 36 is in the extended position (FIG. 2A) to protect the tip portion, but along or about the longitudinal length of the emitter 36 when the sheath 36 is in the retracted position (FIG. 2B) to expose the tip portion thereof.

As shown in FIGS. 2A and 2B, the sheath 16 may be configured to translate along the longitudinal length or direction of the column 10 between the extended and retracted positions. For example, as shown in FIGS. 2A and 2B the longitudinal length or distance L1 between the tip or end of the sheath 16 and a reference point along the longitudinal length of the column 10 when the sheath 16 is in the extended position is greater than the longitudinal distance L2 between the tip of the sheath 16 and the reference point when the sheath 16 is in the retracted position. The reference point may be any fixed point along the longitudinal length of the column 12. As explained further below, the reference point may be a laterally extending (and/or proximally-facing) surface, edge or feature of the column 10 such that a device may couple to the reference point and the sheath 16 to maintain the sheath 16 in the retracted position (i.e., maintain the longitudinal length L2) when the column 10 is not in use. In some embodiments, the sheath 16 may be positioned in the retracted position (FIG. 2A) such that at least about 4 mm of the tip portion of the emitter 36 is exposed.

The sheath 16 may be spring loaded or otherwise configured such that the sheath 16 is normally biased into the extended position (FIG. 2A) and must be moved and maintained into the retracted position (FIG. 2B) during use. As shown in FIGS. 2A and 2B, the sheath 16 may comprise two components or portions. In some embodiments, the sheath 16 may include first portion 32 that is relatively large or wide in the lateral direction and positioned or arranged adjacent to the metal portion 14, and a second portion 34 that is a relatively small or narrow in the lateral direction as compared to the first portion 32 and positioned or arranged adjacent to, or extending from, the first portion 32 in the longitudinal direction. The second section 34 of the sheath 16 may thereby define the end or tip of the sheath 16 in the longitudinal direction when the sheath 16 is in the extended position (FIGS. 1 and 2A) (and, potentially, define the longitudinal end or tip of the column 16).

In some embodiments, shown in FIGS. 1 and 2, the first and second sheath portions 32, 34 and the metal portion 14 may be configured in a telescoping relationship such that the second sheath portion 34 may translate longitudinally within the first sheath portion 32, and the first sheath portion 34 may translate longitudinally within the metal portion 14. In such an arrangement, in the retracted position the sheath 16 may include the first portion 32 (and, potentially, the second portion 34) at least partially longitudinally retraced or positioned within the metal portion 14, as shown in FIG. 2B. In some embodiments, in the retracted position the sheath 16 may include the second portion 34 at least partially longitudinally retracted or positioned within the first portion 32, as shown also shown in FIG. 2B. In some embodiments, the first and second sheath portions 32, 34 may be overlapping or telescoping cylindrical sections that slide or translate inwardly (retracted position—FIG. 2B) and outwardly (extended position—FIG. 2A). In some such embodiments, the first section 32 may define a larger diameter than the second section 34, and the second section 34 may be positioned partially within the first section 32 (and the first section 32 may be positioned partially within the metal portion 14 of the column 10). For example, the second section 34 may define an outer diameter of about 2 mm and the first section 32 may define an outer diameter greater than about 2 mm (and an inner diameter of about 2 mm or greater to accommodate the second section 34 therein). In some embodiments, the column holding portion 12 (besides the extension portion 22) and the metal portion 14 of the column 10 may each be substantially cylindrical and aligned along a longitudinal axis, and the first and second sheath portions 32, 34 of the sheath 16 may be cylindrical and the longitudinal axes thereof aligned with the longitudinal axis of the column holding portion 12 and the metal portion 14 of the column 10. In this way, the column holding portion 12 (besides the extension portion 22), the metal portion 14 and the first and second sheath portions 32, 34 of the sheath 16 may aligned such that they share the same longitudinal axis.

Figure 3:
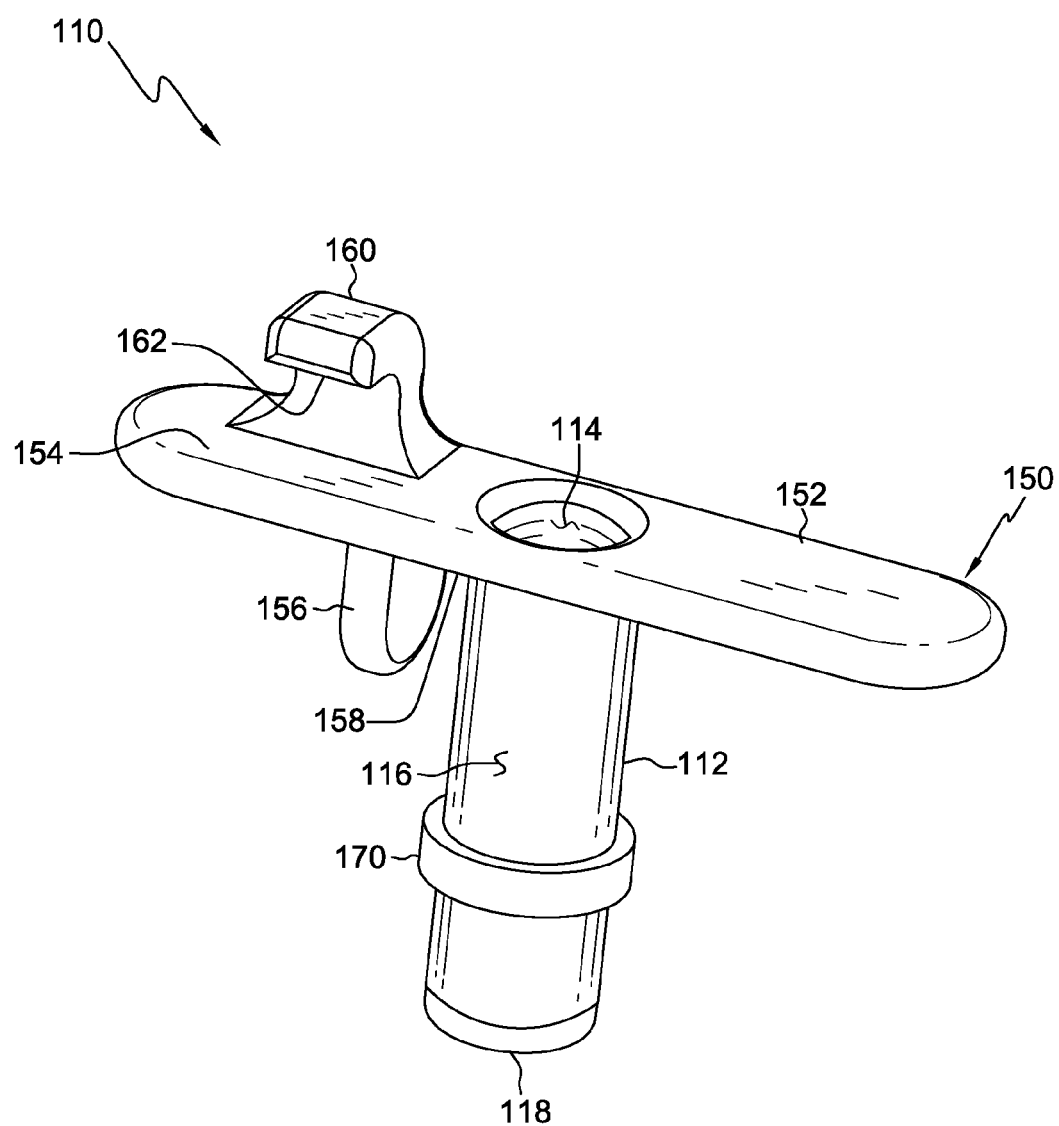
FIG. 3 is a perspective view of an exemplary electrospray column treatment device in accordance with an exemplary embodiment of the present disclosure.

An exemplary embodiment of a device for facilitating treatment of a column, such as the exemplary embodiments of the column 10 of FIGS. 1-2B described above, is shown in FIGS. 3-7 and referenced generally by reference numeral 110. As shown in FIGS. 3-6 the exemplary device 110 includes an exemplary elongate support member 112 including an exemplary interior surface 114 and an exemplary exterior surface 116. The support member 112 may be elongate in the longitudinal direction. As shown in FIGS. 3 and 6, the longitudinally extending support member 112 may include a concaved arcuate or curved interior surface 114. In some embodiments, the radius of the arcuate interior surface 114 may be substantially similar to the radius of the exterior surface of the column 10 (e.g., a convex exterior surface of the metal portion 14 and/or column holding portion 12). In other embodiments the interior surface 114 of the support member 112 of the device 110 may not be arcuate, but may be flat or include any other shape, pattern or arrangement. For example, the interior surface 114 of the support member 112 of the device 110 may be any configuration capable of supporting or otherwise engaging at least a portion of the exterior surface of the exemplary column 10 (e.g., the exterior surface of the metal portion 14 and/or column holding portion 12) when the column 10 and device 110 are coupled (as described further below). In other embodiments, the interior surface 114 of the support member 112 of the device 110 may not support or otherwise engage at least a portion of the exterior surface of the exemplary column 10 (e.g., the exterior surface of the metal portion 14 and/or column holding portion 12) when the column 10 and device 110 are coupled.

Figure 5:
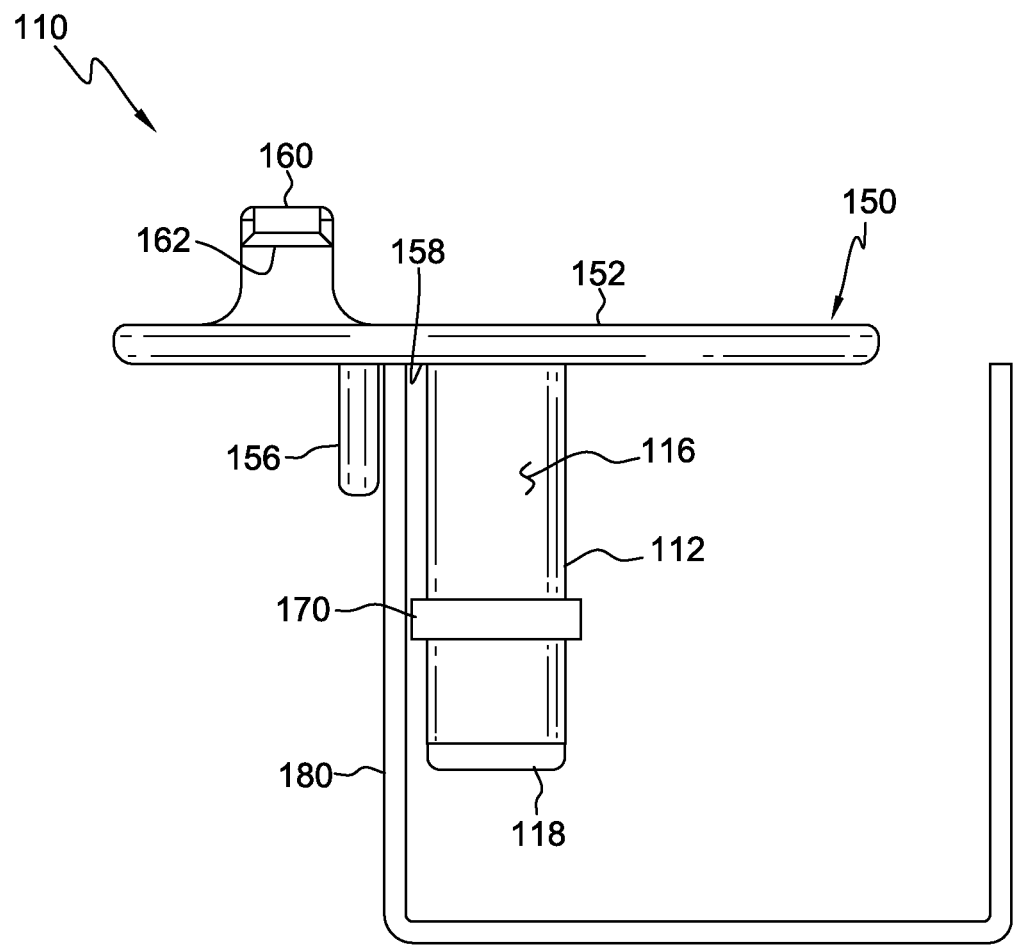
FIG. 5 is a side view of the exemplary electrospray column treatment device of FIG. 3 coupled to an exemplary substrate in accordance with an exemplary embodiment of the present disclosure.
Figure 6:
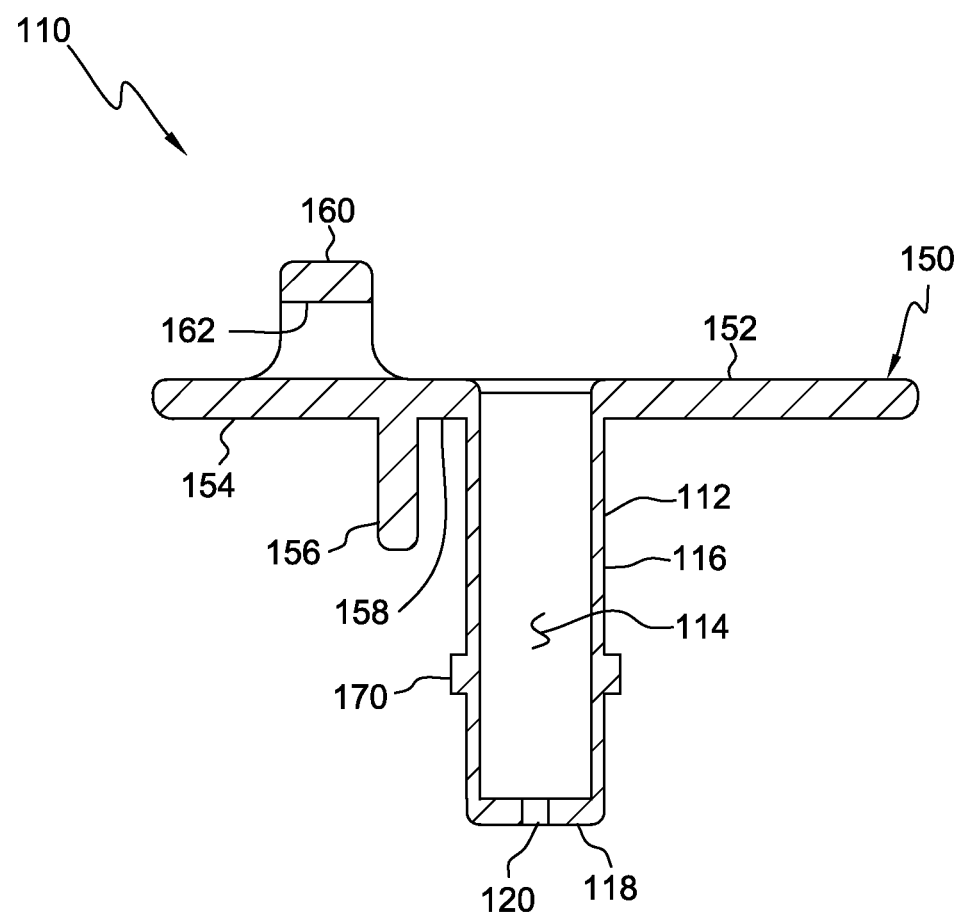
FIG. 6 is a side cross-sectional view of the exemplary electrospray column treatment device of FIG. 3 in accordance with an exemplary embodiment of the present disclosure.
Figure 7:
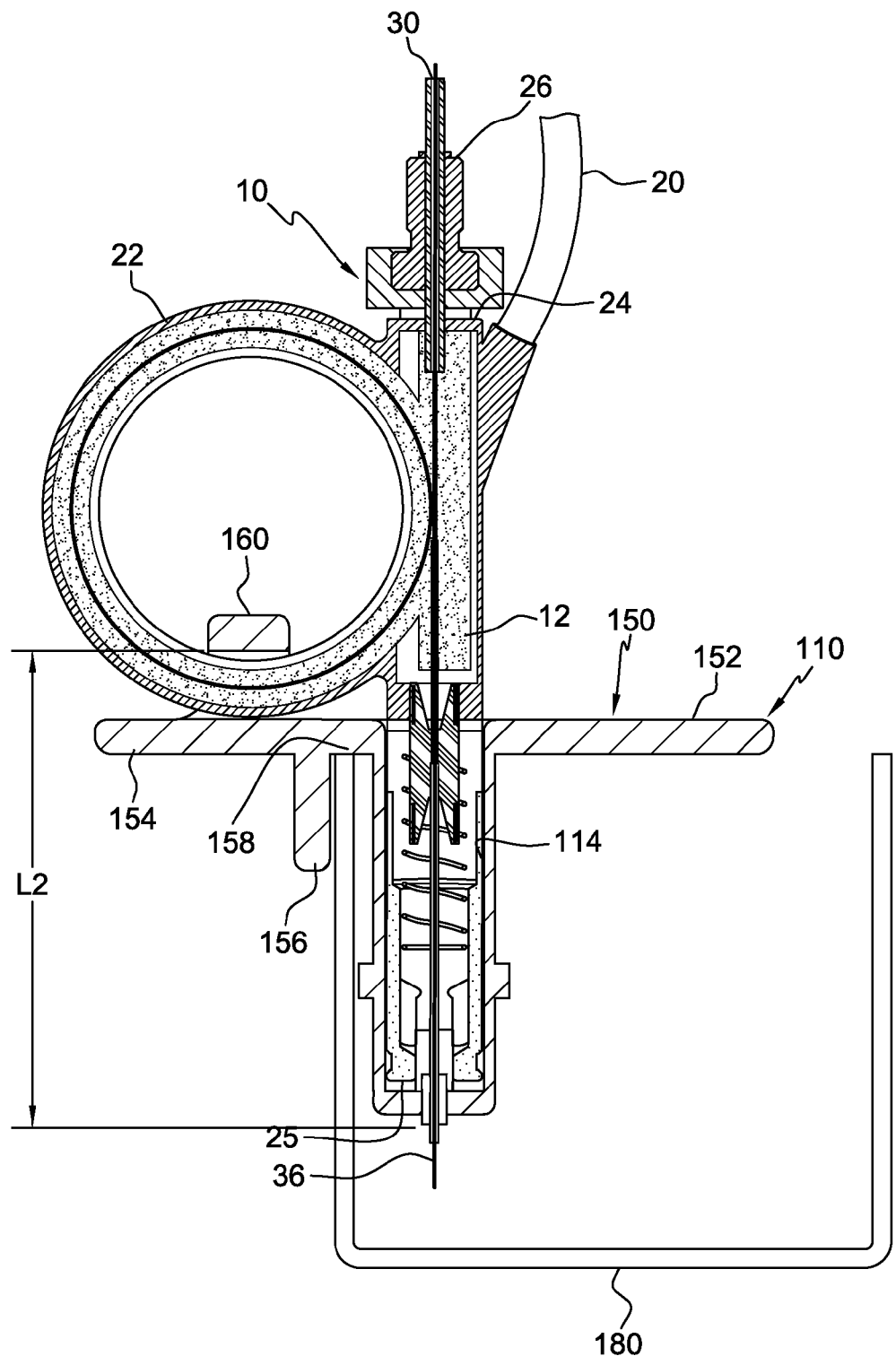
FIG. 7 is a side cross-sectional view of the exemplary electrospray column treatment device of FIG. 3 coupled with the exemplary electrospray column of FIG. 1, and positioned on an exemplary substrate in accordance with an exemplary embodiment of the present disclosure.

In the exemplary embodiment shown in FIGS. 3-6, the interior surface 114 of the support member 112 is cylindrical and thereby forms a cylindrical void or space for accepting at least a portion of the metal portion 14 (and, potentially, at least a portion of the column holding portion 12) of the column 10 within the cylindrical void or space. For example, in some embodiments the cylindrical void may have a radius of about 8.5 mm, and the metal portion 14 (and, potentially, at least a portion of the column holding portion 12) may define a radius of about 9 mm. In some such embodiments, as shown in FIG. 7, the sheath 16 portion (and emitter 36 therein) and at least a portion of the metal portion 14 (and, potentially, at least a portion of the column holding portion 12) may be inserted longitudinally into the cylindrical void or space formed by the interior surface 114 of the support member 112 during use.

Figure 4:
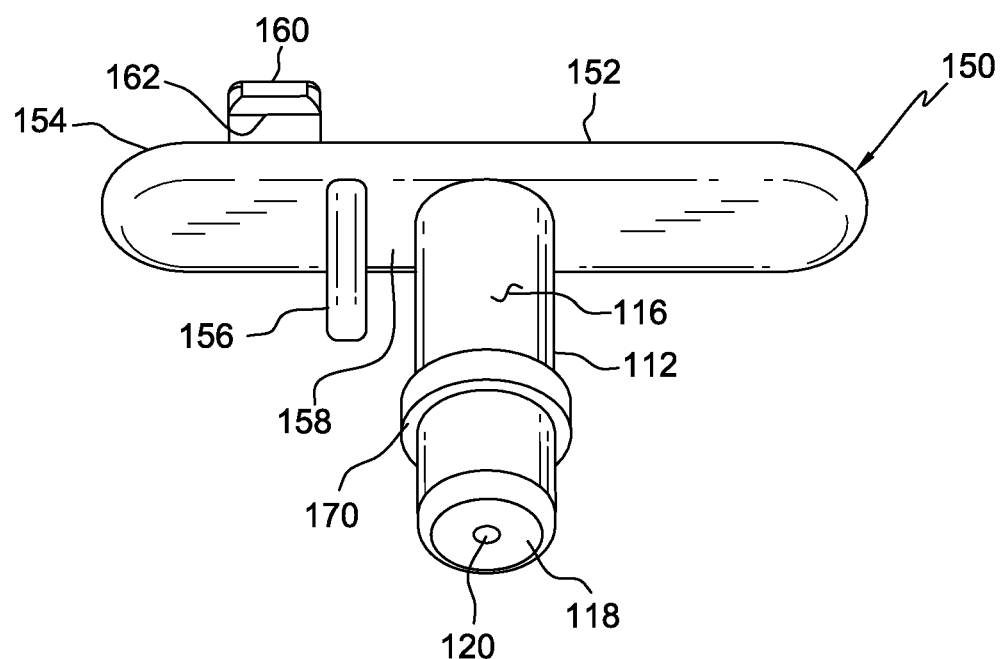
FIG. 4 is a perspective view of the exemplary electrospray column treatment device of FIG. 3 in accordance with an exemplary embodiment of the present disclosure.

In some embodiments, a distal end or portion of the support member 112 may include a sheath engagement member 118 as shown in FIGS. 4 and 6. The sheath engagement member or portion 118 may extend at least generally laterally from the inner or interior surface 114 of the longitudinally elongate or extending support member 112, as shown in FIG. 4. In some embodiments, the sheath engagement member 118 may define the distal end of the longitudinally elongate or extending support member 112. The sheath engagement member 118 may include one or more surface, edge, member or other feature or aspect 120 that is configured to engage the exterior surface (and/or a lateral surface or aspect) of the protective sheath 16 of the column 10 when the device 110 is coupled to the column 10. In some embodiments the portion or aspect of the sheath engagement member 118 configured to engage, and thereby retract, the protective sheath 16 of the column 10 may be sized and shaped substantially similar to the exterior size and shape of a portion of the protective sheath 16. In some embodiments, the aspect of the sheath engagement member 118 that is configured to engage and retract a protective sheath 16 of a column 10 may be configured to engage and retract a particular portion of the sheath 16. For example, the aspect of the sheath engagement member 118 that is configured to engage and retract a protective sheath 16 of a column 10 may be configured to engage and retract a first wide or large portion of the sheath 16. In other embodiments, however, the aspect of the sheath engagement member 118 that is configured to engage and retract the protective sheath 16 of the column 10 may be configured to engage and retract more than one portion of the protective sheath 16, such as both the first narrow portion 32 and second wide portion 34 thereof.

In the exemplary embodiments shown in FIGS. 3-6, the exemplary sheath engagement member 118 includes an exemplary aperture 120 extending through the sheath engagement member 118 in the longitudinal direction configured to engage the sheath 16 of the column 10. As shown in FIG. 4, the exemplary aperture 120 extending through the sheath engagement member 118 is circular or cylindrical. The center or axis of the aperture 120 may be aligned with the longitudinal axis of the radius of the interior surface of the support member. In some such embodiments, the cylindrical exemplary aperture 120 may be configured to engage an outer surface of the substantially cylindrical sheath 16 of a column 10, as shown in FIG. 7. In some such embodiments, the radius of the cylindrical exemplary aperture 120 may be substantially similar to a radius of the exterior surface of a portion of the sheath 16. For example, as shown in the cross-sectional view of FIG. 7, the aperture 120 of the sheath engagement member 118 may include a radius substantially similar to the radius of the exterior surface of the second narrower portion 34 of the protective sheath 16 of the exemplary column of FIGS. 1-2B. As a result, the radius of the aperture 120 of the sheath engagement member 118 may be relatively smaller or narrower than the radius of the exterior surface of the first wide portion 32 of the protective sheath 16. In this way, as shown in FIG. 7, when the device 110 and column 10 are coupled and the sheath 16 is inserted into the aperture 120 of the sheath engagement member 118, the second narrow portion 34 of the protective sheath 16 may extend into (and potentially through) the aperture 120 but the first wide portion 32 of the protective sheath 16 may be too wide or large in the lateral direction to fit within the aperture 120. The sheath engagement member 118 may thereby engage the first wide or large portion 32 of the protective sheath 16 and longitudinally retract the protective sheath 16 to expose the tip portion of the emitter 36 on the distal side of the sheath engagement member 118 while leaving the second narrow or small portion 34 of the sheath 16 about the emitter 16 within the aperture 120 when the device 110 and column 10 are coupled, as shown in FIG. 7. In such an embodiment, the device 110 advantageously prevents the sheath engagement member 118 from contacting and potentially damaging the emitter 36 when the device 110 and column 10 are coupled as the second narrow or small portion 34 of the sheath 16 remains about the emitter 36 within the aperture 120, as shown in FIG. 7.

The sheath engagement member 118 may retract the first wide or large portion 32 of the protective sheath 16 when the device 110 and column 10 are coupled by engaging a longitudinally extending surface of the first wide or large portion 32 of the protective sheath 16 and/or laterally extending surface of the first wide or large portion 32 of the protective sheath 16. For example, a proximal-facing surface of the sheath engagement member 118, such as a proximal-facing surface or edge about the aperture 120, may engage a distal-facing surface or edge of the first wide or large portion 32 of the protective sheath 16 when the device 110 and column 10 are coupled, as shown in FIG. 7.

As also shown in FIG. 7, the relative longitudinal lengths of the second narrow or small portion 34 of the sheath 16 and sheath engagement member 118 may be configured such that the narrow or small portion 34 of the sheath 16 passes through or over the entirety of the sheath engagement member 118 when the device 110 and column 10 are coupled. For example, in some embodiments the sheath engagement member 118 at the aperture 120 may be about 2 mm thick in the longitudinal direction, and the second narrow portion 34 of the sheath 16 may be about 4 mm to about 5 mm thick in the longitudinal direction. In other exemplary embodiments, the relative longitudinal lengths of the second narrow or small portion 34 of the sheath 16 and sheath engagement member 118 may be configured such that only a portion of the longitudinal length of the narrow or small portion 34 of the sheath 16 passes through or over the sheath engagement member 118 when the device 110 and column 10 are coupled.

In some embodiments, the device 110 may be configured such that the interior surface 114 of the support member 112 of the device 110 is effective in guiding the sheath 16 of the column 10 against the sheath engagement member 118 (e.g., within or against the aperture 120 or other engagement surface or aspect of the sheath engagement member 118). For example, the cylindrical void or space formed by the interior surface 114 of the support member 10 and the aperture 120 may be configured such that when the sheath 16 (with emitter 36 therein) and at least a portion of the metal portion 10 (and, potentially, at least a portion of the column holding portion 12) is inserted into the cylindrical void or space, the sheath 16 is automatically substantially aligned with the aperture 120 of the sheath engagement member 118.

As shown in FIGS. 3-6, the device 110 includes a handle portion or member 150. The handle member 150 may be coupled to a proximal portion or end of the support member 112. In some embodiments, as shown in FIG. 6, the handle member 150 and the support member 112 are integral or of one-piece construction. In the exemplary embodiment shown in FIGS. 3-6, the handle member 150 is formed about the support member 112 such that the interior surface 114 of the support member 112 may be accessed from the proximal end or side of the support member 112. The handle member 150 may extend at least generally laterally at least to one side of the support member 112. In the exemplary illustrated embodiment, the handle member 150 includes portions that extend on opposing lateral sides of the support member 112 such that the handle member 150 and the support member 112 form a "T" shape, as shown in FIGS. 3-6. As shown in FIGS. 3-6, a first portion 152 of the handle member 150 may extend substantially laterally from the support member 112 on a first lateral side thereon. The first portion 152 of the handle member 150 (and/or, potentially, the first portion 154) may be utilized as a manual engagement handle or portion of the device 110 during use. For example, a user may manually engage the first portion 152 (and/or the second portion 154) of the handle member 150 of the device 110 with one hand and utilize the other hand to insert the column 10 against the interior surface 114 of the support member 112 such that the sheath engagement member 118 engages and retracts the sheath 16 to expose the tip portion of the emitter 36.

In some exemplary embodiments, the handle member 150 may include a second portion 154. The second portion 154 may extend from a lateral side of the support member 112. The second portion 154 may include a second longitudinally extending member or portion 156 as shown in FIGS. 3-6. The second longitudinally extending member or portion 156 may be a distinct component coupled to the second lateral portion 154 or integral therewith (i.e., of one-piece construction). The second longitudinally extending member or portion 156 may extend generally longitudinally from a distal-facing portion or surface of the second lateral portion 154 toward the sheath engagement member 118, as shown in FIG. 4. The second longitudinally extending member or portion 156 may extend generally longitudinally along at least a portion of the longitudinal length of the support member 112 as shown in FIGS. 3-6. The second longitudinally extending member or portion 156 may be spaced laterally from the support member 112 such that a first lateral portion 158 of the second lateral member 154 extends at least generally laterally between the support member 112 and the second longitudinally extending member or portion 156.

As shown in FIGS. 5 and 7, the second longitudinally extending member or portion 156, first lateral portion 158 and support member 112 may form an edge grabber or handle feature that enables the device 10, and potentially the column 10 coupled thereto, to couple to the sidewall of a container 180 or other longitudinally extending surface or element. For example, with reference to FIGS. 5 and 7 the longitudinally extending support member 112 may extend down the interior side of a sidewall of the container 180 (or other longitudinally shaped element), and the second longitudinally extending member 156 of the second lateral portion 154 may extend down the exterior side of the sidewall of the container 180. As also shown in FIGS. 5 and 7, the first lateral portion 158 of the second lateral member 154 extending between the support member 112 and the second longitudinally extending member 156 may abut the top edge or surface of the sidewall of the container 180, and thereby act to suspend the device 110 on the side wall such that the sheath engagement member 118 and the tip portion of the emitter 36 of the column 10 coupled thereto is held or suspended above the bottom of the container 180. For example, the distal-facing surface of the first lateral portion 158 of the second lateral member 154 may abut the top edge or surface of a longitudinally extending substrate, such as the sidewall of a container 180.

As shown in FIG. 7, the handle feature of the device 110 allows the exposed tip portion of a column 10 coupled thereto to be suspended in a container 180 filled with a treatment liquid or like material for inspection and/or treatment. Similarly, the handle feature of the device 110 allows the column 10 coupled thereto to be suspended on a longitudinally extending substrate with the tip portion of the emitter 36 exposed for inspection and/or treatment. To further aid the placement, suspension or coupling of the device 110, and a column 10 coupled thereto, to a longitudinally extending substrate (e.g., a sidewall of a container 180), the support member 112 may include one or more laterally extending projection or stand-off 170, as show in FIGS. 3-6.

With reference to FIGS. 5 and 7, the laterally extending projection 170 may be a distinct component coupled to the support member 112 or may be integral with the support member 112 (i.e., of one-piece construction). The projection 170 may extend at least generally laterally away from the exterior surface 112 (and interior surface 114) of the support member 112. The projection 170 may be longitudinally positioned further distally than the longitudinal length of the longitudinally extending member 156, as shown in FIGS. 5 and 6. In alternative embodiments, the projection 170 may be adjacent, at least partially, to the longitudinally extending member 156 in the longitudinal direction. As shown in FIGS. 5 and 7, the projection 170 may operate in concert with the handle portion of the device 110 when the device 110 (and a column coupled thereto) is positioned over or on a longitudinally extended substrate such as a sidewall of a container 180. The projection 170 may abut the interior surface of the longitudinally extended substrate 180 (such as a sidewall of a container) to space the distal sheath engagement member 118, and thereby the tip portion of an emitter 36 of a column 10 coupled thereto, from the interior surface of the substrate 180. Further, the projection 170 may act in concert with the longitudinally extending member 156 to limit the lateral spacing between the exterior surface of the projection 170 and the interior surface of the longitudinally extending member 156 so a longitudinally extended substrate 180 can fit relatively snuggly therebetween. The relatively narrow lateral spacing between the exterior surface of the projection 170 and the interior surface of the longitudinally extending member 156 (in comparison to the width or thickness of the substrate 180), may act to prevent, or at least limit, the device 110 from being positioned angularly toward the interior surface of the substrate 180 from the proximal end to the distal sheath engagement member 118 of the device 10. In this way, the projection 170 may prevent the tip portion of an emitter 36 of a column 10 coupled to the device 110 from being angled toward the interior surface of the substrate 180 and, potentially, contact the interior surface of the substrate 180.

As shown in FIGS. 3-7, the exemplary device 110 may include a lateral surface coupling member or portion 160. The lateral surface coupling member or portion 160 may be a distinct component coupled to the device 10, or may be integral with another component or aspect of the device 10. In the exemplary embodiments shown in FIGS. 3-7, the coupling member 160 is provided on the proximal-side of the second lateral member 154 of the handle member 150. In some embodiments, the coupling member 160 may be any shape, size, position or arrangement such that the coupling member 160 includes at least one coupling surface or edge 162 that faces or opposes the direction that the sheath or sleeve 16 moves from the retracted position (e.g., FIG. 2A) to the extended position (e.g., FIG. 2B). The coupling surface or edge 162 of the coupling member 160 may thereby be utilized to contact a portion of a column 10 coupled to the device 110 such that the sheath 16 is retracted (e.g., via the sheath engagement member 118) to temporality maintain the retracted position of the sheath 16. For example, a column 10 may be coupled to the device such that the sheath engagement member 118 of the device 110 retracts the sheath 16 to expose the tip portion of the emitter 36. In such an arrangement, the device 110 and the column 10 may be positioned relative to each other such that the coupling surface or edge 162 abuts against a portion of the column 10 to further couple the device 110 and column 10 and prevent any biasing force of the sheath 16 from repositioning the column 10 and/or device 110 such that the sheath 16 moves from the retracted position to an extended position (and thereby cover or otherwise shield the tip portion of the emitter).

In the exemplary embodiment shown in FIGS. 1-2A, the sheath 16 of the device 110 moves or translates at least generally in the longitudinally direction between a proximal position in the retracted state and a distal position in the extended state. In some such embodiments, the coupling member 160 may be any shape, size, position or arrangement such that the coupling member 160 is positioned proximal of the sheath engagement member 118 in the longitudinal direction and includes at least one distal-facing (in the longitudinal direction) surface or edge 162, as shown in FIGS. 3-7. Stated differently, in some such embodiments the coupling member 160 may include a coupling surface or edge 162 that is positioned proximal of the distal sheath engagement member 118 in the longitudinal direction and faces at least generally distally in the longitudinal direction. As described above, in such an arrangement the at least generally distally facing coupling surface or edge 162 of the coupling member 160 can be utilized to prevent the sheath 16 from longitudinally translating from the proximal retracted position (see FIG. 2B) to the distal extended position (see FIG. 2A) to maintain exposure of the tip portion of the emitter 36 of the column 10.

In the embodiment shown in FIGS. 3-7, the coupling member 160 includes a projection extending from the proximal-side of the second lateral member 154 of the handle member 150 in the proximal direction (at least generally longitudinally). The coupling member 160 generally defines an "L" shape such that the distally-facing coupling surface or edge 162 of the coupling member 160 is spaced longitudinally from the proximal-side of the second lateral member 154, thereby providing clearance or space below the coupling surface or edge 162 in the distal direction to allow a portion of a column to positioned therein, as shown in FIG. 7. As shown in FIG. 7, the device 110 may be configured such that the coupling surface or edge 162 of the coupling member 160 engages or abuts a proximal-facing surface or edge of the extension portion 22. For example, in embodiments in which the extension portion 22 forms or includes an aperture therethrough, the coupling surface or edge 162 of the coupling member 160 may engage or abut a proximal-facing surface or edge of the interior of the aperture of the extension portion 22, as show in FIG. 7. As described above, in such an arrangement the coupling member 160 may couple the device 110 and a column 10 to one another and prevent the device 110 and a column 10 from translating the longitudinal direction such that the sheath 16 of the column 10 and the sheath engagement member 118 of the device 110 move apart (in the longitudinal direction) and allow the sheath 16 to move from the retracted position (see. FIG. 2B) to the extended position (see. FIG. 2A). In this way, the coupling member 160 may operate or act in concert with the sheath engagement member 118 to at least maintain the retracted state of the sheath 16 and expose the tip portion of the emitter 36 (see. FIG. 2B).

A second embodiment of an exemplary device for facilitating treatment of a column, such as the exemplary embodiments of the column 10 of FIGS. 1-2B described above, is shown in FIGS. 8-13 and referenced generally by reference numeral 210. The exemplary device 210 is similar to the exemplary device 110 described above and shown in FIGS. 3-7 and therefore like reference numerals preceded by the numeral "2," as opposed to "1," are used to indicate like elements. The description above with respect to the device 110, including description regarding alternative embodiments (i.e., modifications, variations or the like), equally applies to device 210 (and any alternative embodiments thereof). As shown in FIGS. 8-13, inter alia, the exemplary device 210 differs from the exemplary device 110 of FIGS. 3-7 in the configuration, arrangement and/or orientation of several components or aspects.

Figure 10:
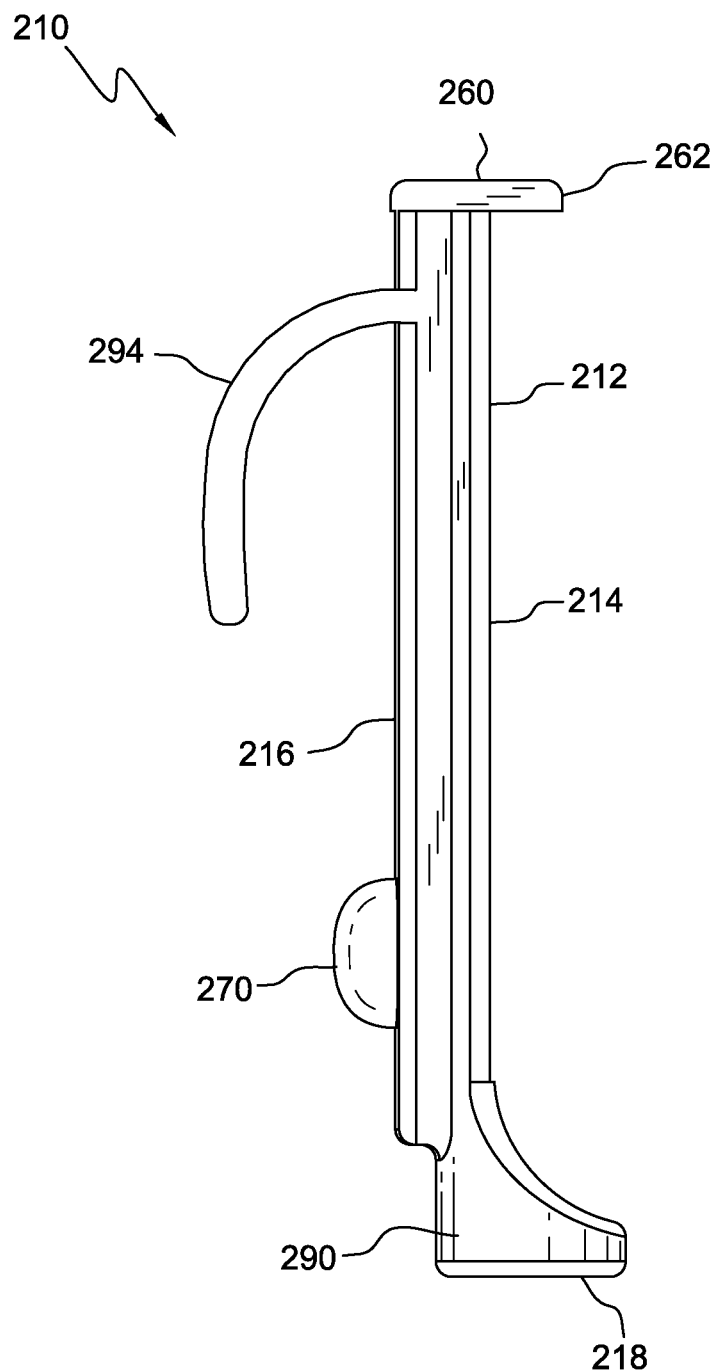
FIG. 10 is a side view of the exemplary electrospray column treatment device of FIG. 8 in accordance with an exemplary embodiment of the present disclosure.
Figure 11:
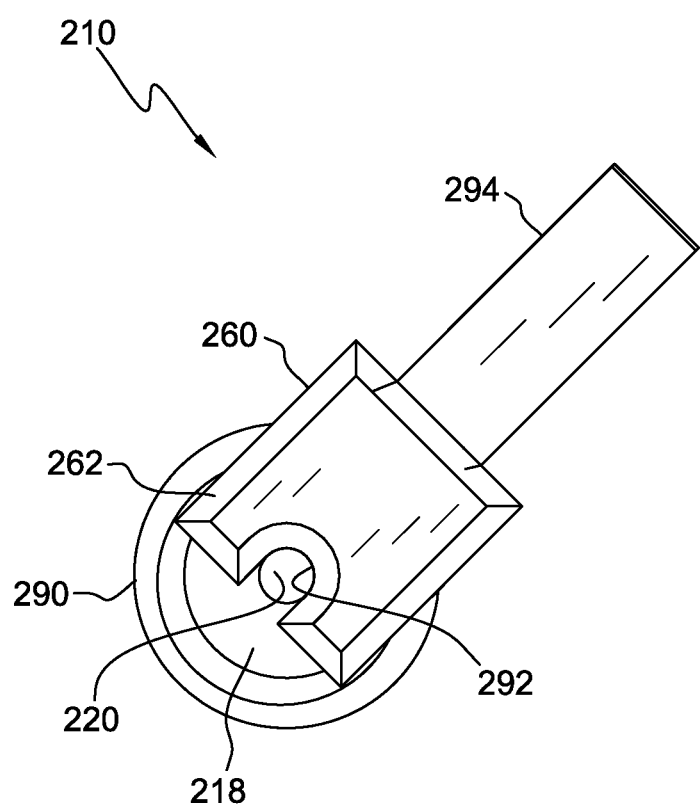
FIG. 11 is a top view of the exemplary electrospray column treatment device of FIG. 8 in accordance with an exemplary embodiment of the present disclosure.
Figure 12:
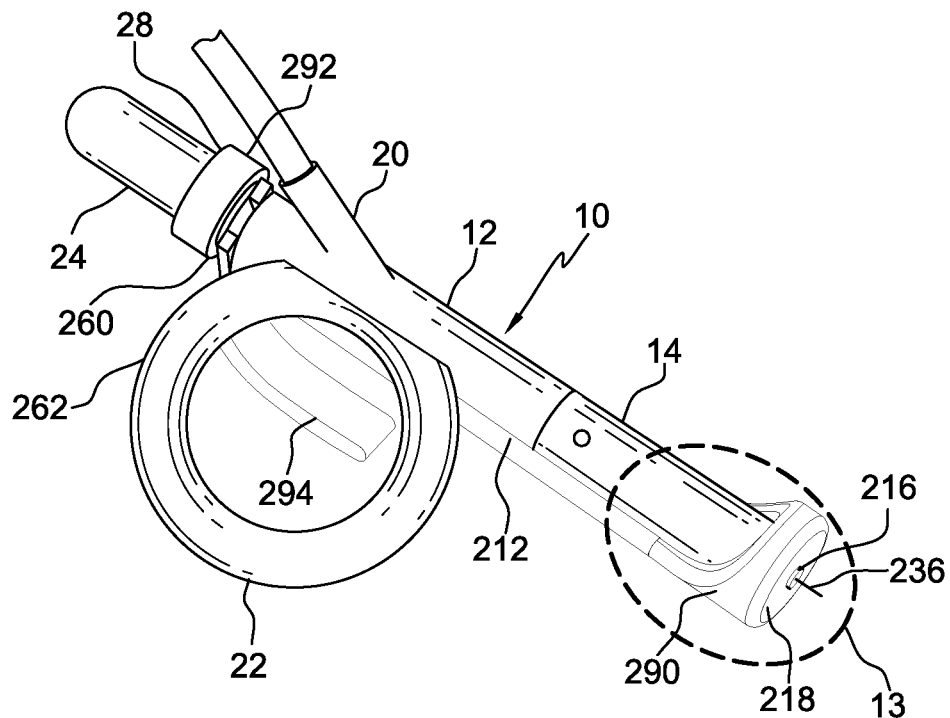
FIG. 12 is a perspective view of the exemplary electrospray column treatment device of FIG. 8 coupled with the exemplary electrospray column of FIG. 1.
Figure 13:
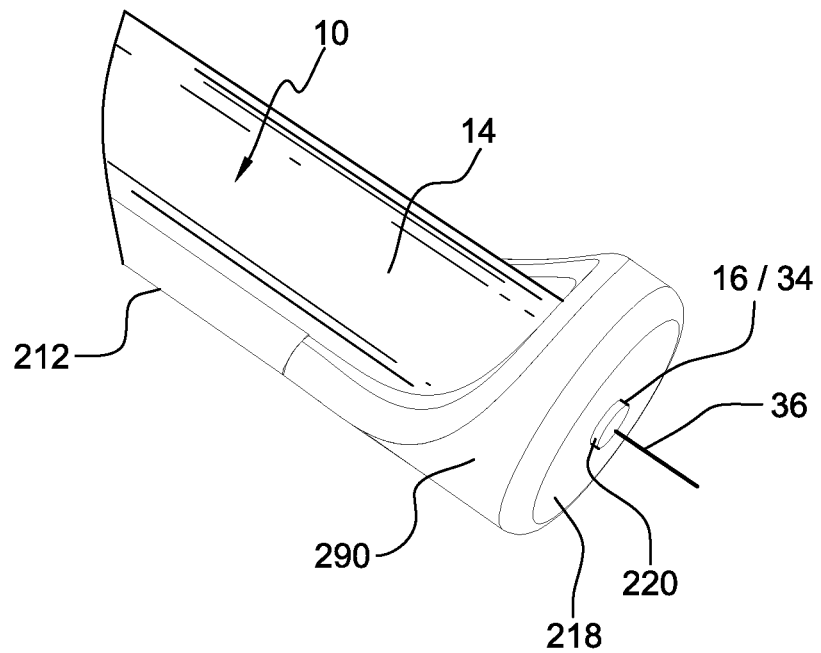
FIG. 13 is a perspective view showing an exemplary sheath engagement member of the exemplary electrospray column treatment device of FIG. 8 retracting an exemplary protective sheath of the exemplary electrospray column of FIG. 1.

As shown in FIGS. 8-13, the interior or inner surface 214 of the support member 212 is arcuate and defines an open or exposed surface, as opposed to an aperture or void. As shown in FIG. 12, the interior surface 214 of the support member 212 of the device 210 may abut or cradle a lateral side surface of a column 10 when the column 10 and device 210 are coupled. As also shown in FIGS. 8-13, the support member provides a rim portion 290 about the sheath engagement member 218 at the distal end or portion of the device 210. The inner surface of the rim portion 290 may extend from the interior surface 214 of the support member 212 and about the sheath engagement member 218 to form a cylindrical or circular void at the proximal side of the sheath engagement member 218. In use, the device 210 may be angularly oriented with respect to the column 10 and the distal end 25 of a column 10 may be inserted into the cylindrical or circular void formed by the inner surface of the rim portion 290 and the interior surface 214, as shown in FIGS. 12 and 13. As shown in FIG. 12, the sheath 16 of the column 10 may then be positioned against the sheath engagement member 218 (e.g., through the aperture 220), and the column 10 may be distally translated (longitudinally) and angled with respect to the device 110 such that the laterally extending distal surface 25 of the column 10 abuts the proximal-facing surface of the sheath engagement member 218 (and temporality retracts the sheath 16) and a lateral side surface of the columns 10 (e.g., a lateral side surface of the metal portion 14 and/or the column portion 12) abuts the interior surface 214 of the support member 212.

Figure 8:
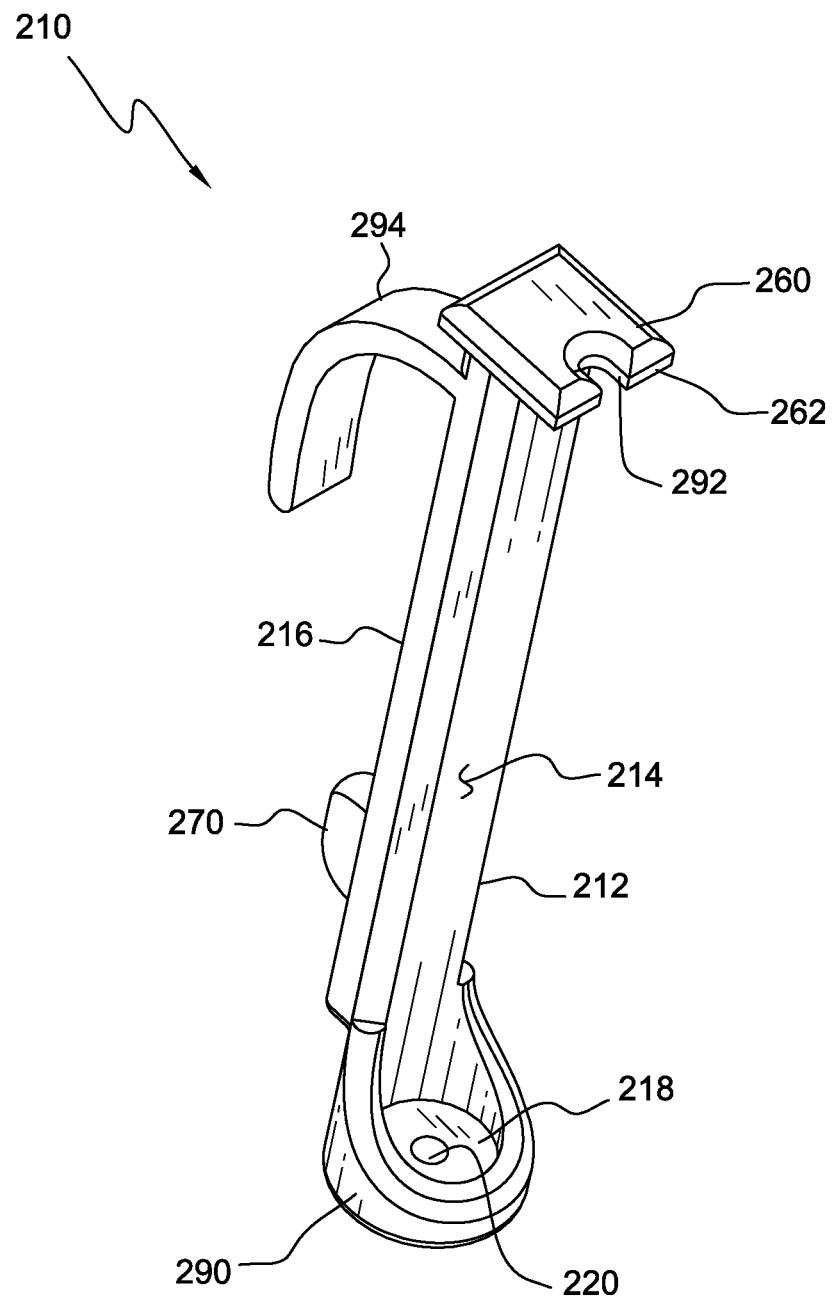
FIG. 8 is a perspective view of an exemplary electrospray column treatment device in accordance with another exemplary embodiment of the present disclosure.
Figure 9:
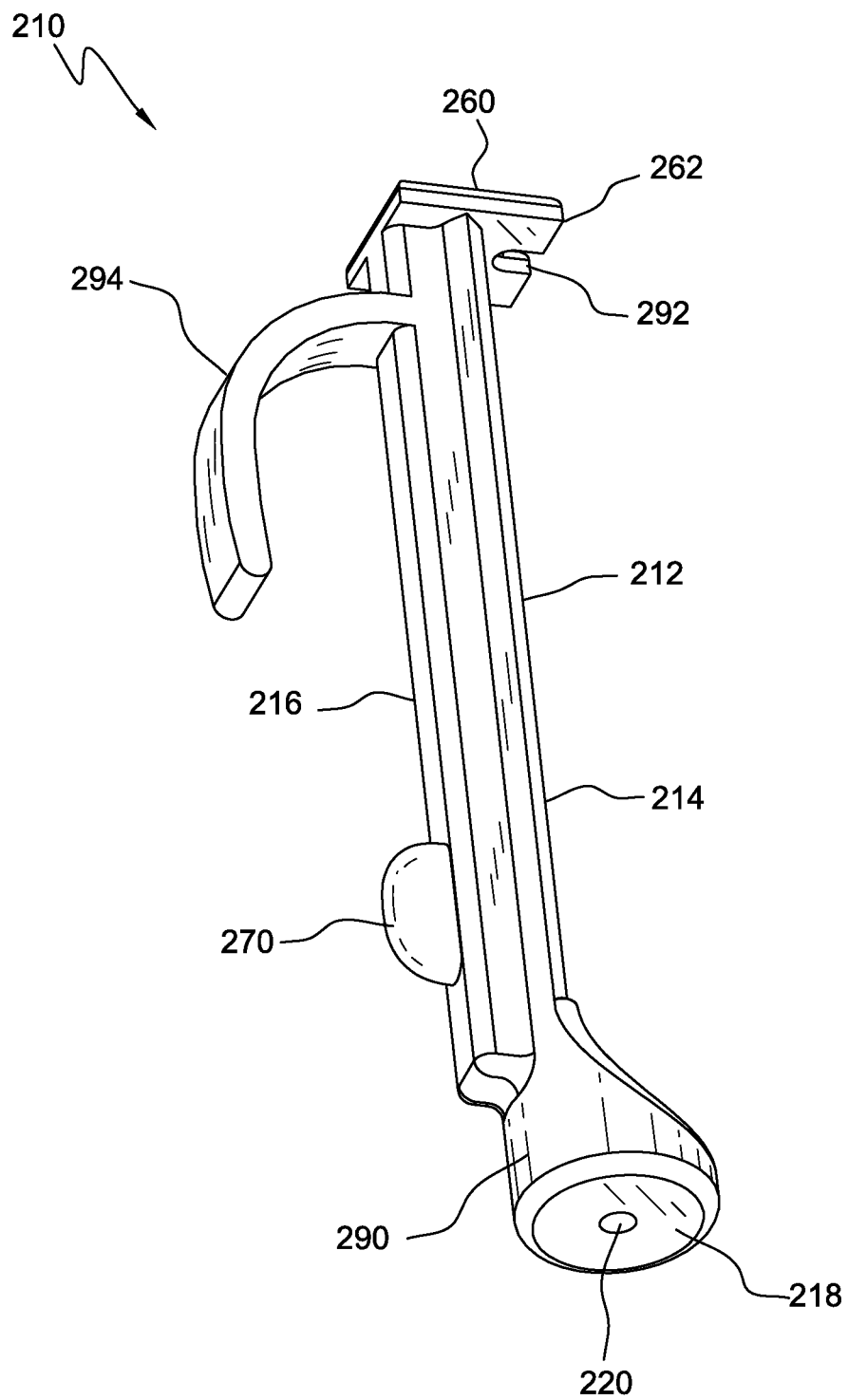
FIG. 9 is a perspective view of the exemplary electrospray column treatment device of FIG. 8 in accordance with an exemplary embodiment of the present disclosure.

With reference to FIGS. 8-12, the coupling member 260 of the device 210 is provided on a proximal end or portion of the support member 212. The coupling member 260 extends laterally from the support member 212 at least towards and past the interior surface 214 of the support member 212, as shown in FIGS. 8-10. In this way, the coupling surface 262 of the coupling member 260 may be substantially longitudinally aligned with the sheath engagement member 218. As shown in FIGS. 8-10 the coupling member 260 may be provided at the proximal end of the interior surface 214 of the support member 212 and the sheath engagement member 218 may be provided at the distal end of the interior surface 214 of the support member 212. The distal-facing coupling surface or edge 262 of the coupling member 260 and the proximal-facing surface of the sheath engagement member 218 may be substantially parallel.

As shown in FIGS. 8 and 11, the coupling member 260 may include a relief, aperture or the like 292. The relief 292 may be laterally extending. In some embodiments, as shown in FIG. 11, the relief 292 may be longitudinally aligned with the portion of the sheath engagement member 218 than engages the sheath 16 of a column 10, such as the aperture 220, when the column 10 and the device 220 are coupled. For example, as shown in FIG. 11 the relief 292 may be aligned with the axis of the aperture 220 of the sheath engagement member 218. The relief 292 may accommodate one or more aspects or elements of a column 10 when the column 10 and device 210 are coupled. For example, as shown in FIG. 12 the device 210 may be configured such that when the device 210 and a column 10 are coupled the laterally extending, distal-facing coupling surface 262 of the coupling member 260 abuts the first laterally extending proximal surface 224 of the column and the relief 292 accommodates the fitting portion 18 (e.g., the threaded portion 26 thereof) extending from the proximal surface 24 of the column 10. In such an arrangement, the device 210 may retract the sheath 16 of the column 10 to expose the tip portion of the emitter 36 (see FIG. 13) and maintain the retracted state by longitudinally coupling, constricting, or constraining the column 10 between the coupling member 260 and the sheath engagement member 218. Any potential biasing force of the sheath 18 tending to translate the sheath 16 longitudinally from the retracted position to the extended position is thereby constrained or counteracted by the device 210.

The exemplary device 210 includes a substantially arcuate member 294 that, in combination with the exterior side or surface 216 of the support member 212, forms an edge grabber or handle feature that enables the device 210, and a column 210 coupled thereto, to couple to the sidewall of a container or other longitudinally extending surface or element. As shown in FIGS. 8-10, the arcuate member 294 is positioned proximally and includes or defines a lateral direction or portion that extends away from the exterior side or surface 216 of the support member 212, and includes or defines a longitudinal direction or portion that extends distally toward the sheath engagement member 218. In use, the exterior side surface 216 of the support member 212 may extend down the interior side of a side wall of a container (or other longitudinally shaped element) (e.g., distally), and the arcuate member 294 may extend over the top edge of the container (e.g., laterally) and down the exterior side of the side wall of the container 180 (e.g., distally). In this way, the arcuate member 294 and the support member 212 may form an edge grabber or handle feature that enables the device 210, and a column 210 coupled thereto, to couple to a sidewall of a container or other longitudinally extending surface or element.

The arrangements and/or shapes of the components discussed or illustrated herein are only illustrative for the understanding of the devices and methods; and are not meant to limit the scope of the disclosure. The exact shape, position, arrangement, orientation, material, composition and the like of the components may vary as is known in the art.

It is to be understood that the above description is intended to be illustrative, and not restrictive. Numerous changes and modifications may be made herein by one of ordinary skill in the art without departing from the general spirit and scope of the invention as defined by the following claims and the equivalents thereof. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Also, the term "operably" in conjunction with terms such as coupled, connected, joined, sealed or the like is used herein to refer to both connections resulting from separate, distinct components being directly or indirectly coupled and components being integrally formed (i.e., one-piece, integral or monolithic). Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure. It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the disclosure may include only some of the described embodiments. Accordingly, the invention is not to be seen as limited by the foregoing description, but is only limited by the scope of the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

I claim:

1. A device for facilitating treatment of an electrospray column with a protective sheath that protects a tip portion of an emitter of the column in a first longitudinally extended position and exposes the tip portion in a second longitudinally retracted position, the device including:
    a substantially longitudinally extending support member;
    a sheath engagement member at a distal portion of the support member, the sheath engagement member configured to engage the protective sheath of the column,
    a column engagement member at a proximal portion of the support member, the column engagement member configured to engage a laterally extending portion of the column,
    wherein the longitudinal spacing of the sheath engagement member and the column engagement member is configured to position the protective sheath in the second longitudinally retracted position to expose the tip portion of the emitter of the column when the sheath engagement member engages the protective sheath of the column and the column engagement member engages the laterally extending portion of the column.

2. The device of claim 1, wherein the longitudinally extending support member includes an interior surface configured to engage an exterior surface of the column when the sheath engagement member and the column engagement member engage their respective portions of the column.

3. The device of claim 2, wherein the interior surface of the longitudinally extending support member is a substantially laterally-facing arcuate surface.

4. The device of claim 3, wherein the interior surface of the longitudinally extending support member forms a cavity configured to receive a portion of the column therein when the sheath engagement member and the column engagement member engage their respective portions of the column.

5. The device of claim 4, wherein the cavity is substantially cylindrical.

6. The device of claim 1, wherein the sheath engagement member includes an aperture configured to engage the protective sheath of the column.

7. The device of claim 6, wherein the aperture of the sheath engagement member is configured to allow a narrow portion of the protective sheath of the column to least extend into the aperture and to prevent a wide portion of the protective sheath of the column from extending into the aperture.

8. The device of claim 1, wherein the sheath engagement member is substantially laterally extending and configured to engage a laterally extending portion of a wide portion of the protective sheath of the column and allow a narrow portion of the protective sheath extend at least partially pass through the sheath engagement member.

9. The device of claim 1, wherein the sheath engagement member is substantially laterally extending and configured to engage a distal end of the protective sheath of the column.

10. The device of claim 1, wherein the device includes a handle extending from a proximal portion of the support member, wherein the handle extends laterally from a first portion of an exterior surface of the support member and distally toward the sheath engagement member.

11. The device of claim 10, wherein the handle is substantially arcuate.

12. The device of claim 10, wherein the handle includes a substantially laterally extending member and a substantially longitudinally extending member.

13. The device of claim 12, wherein the column engagement member is substantially laterally extending and positioned on the laterally extending member.

14. The device of claim 10, wherein the device includes a laterally extending projection extending from a distal portion of the first portion of the exterior surface of the support member.

15. The device of claim 1, wherein the column engagement member is substantially laterally extending and positioned on a proximal end of the support member.

16. The device of claim 1, wherein the column engagement member includes a substantially laterally extending relief.

17. A method of temporality retracting a protective sheath of an electrospray column to expose a tip portion of an emitter of the column, the method comprising:

providing or obtaining a device including a substantially longitudinally extending support member, a sheath engagement member at a distal portion of the support member, and a column engagement member at a proximal portion of the support member;

engaging a portion of the protective sheath of the column with the column engagement member of the device;

translating at least one of the column and the device with respect to one another such that the sheath engagement member translates the protective sheath into a retracted position that exposes the tip portion of the emitter of the column;

engaging a laterally extending portion of the column with the column engagement member to couple the column and the device with one another and to maintain the protective sheath in the retracted position to expose the tip portion of the emitter of the column.

18. The method of claim 17, wherein engaging a portion of the protective sheath of the column with the column engagement member of the device includes positioning a narrow portion of the protective sheath within an aperture of the column engagement member and engaging a wide portion of the protective sheath with the aperture.

19. The method of claim 17, wherein the device includes a laterally and distally extending handle extending from an external surface of the support member, and wherein the method includes positioning the coupled device and column on a substrate by positioning the handle of the device over a top edge of a substrate such that the exterior surface of the support member is positioned on one side of the substrate and at least a portion of the handle is positioned on an opposing side of the substrate.

20. The method of claim 17, wherein the method includes treating the exposed tip portion of the emitter of the column.

21. The method of claim 17, wherein the laterally extending portion of the column is a proximal end of a holding portion of the column or an extension portion of the holding portion.

* * * * *